US00PP22339P2

(12) United States Plant Patent
Hoefnagels

(10) Patent No.: US PP22,339 P2
(45) Date of Patent: Dec. 13, 2011

(54) ***BEGONIA* PLANT NAMED 'SALSA'**

(50) Latin Name: *Begonia rex*
Varietal Denomination: Salsa

(75) Inventor: Antoon Hoefnagels, Lent (NL)

(73) Assignee: Douglas Cole

( * ) Notice: Subject to any disclaimer, the term of this patent is extended or adjusted under 35 U.S.C. 154(b) by 0 days.

(21) Appl. No.: 12/799,987

(22) Filed: May 5, 2010

(51) Int. Cl.
*A01H 5/00* (2006.01)
(52) U.S. Cl. ..... Plt./343
(58) Field of Classification Search ..... Plt./343
See application file for complete search history.

*Primary Examiner* — June Hwu
(74) *Attorney, Agent, or Firm* — Cassandra Bright

(57) ABSTRACT

A new and distinct *Begonia rex* named 'Salsa' is disclosed, characterized by its vibrant red/purple and silver/green foliage color, medium sized leaves and ease of propagation. The new cultivar is a *Begonia rex* typically suited for ornamental container use.

1 Drawing Sheet

Figure 1:
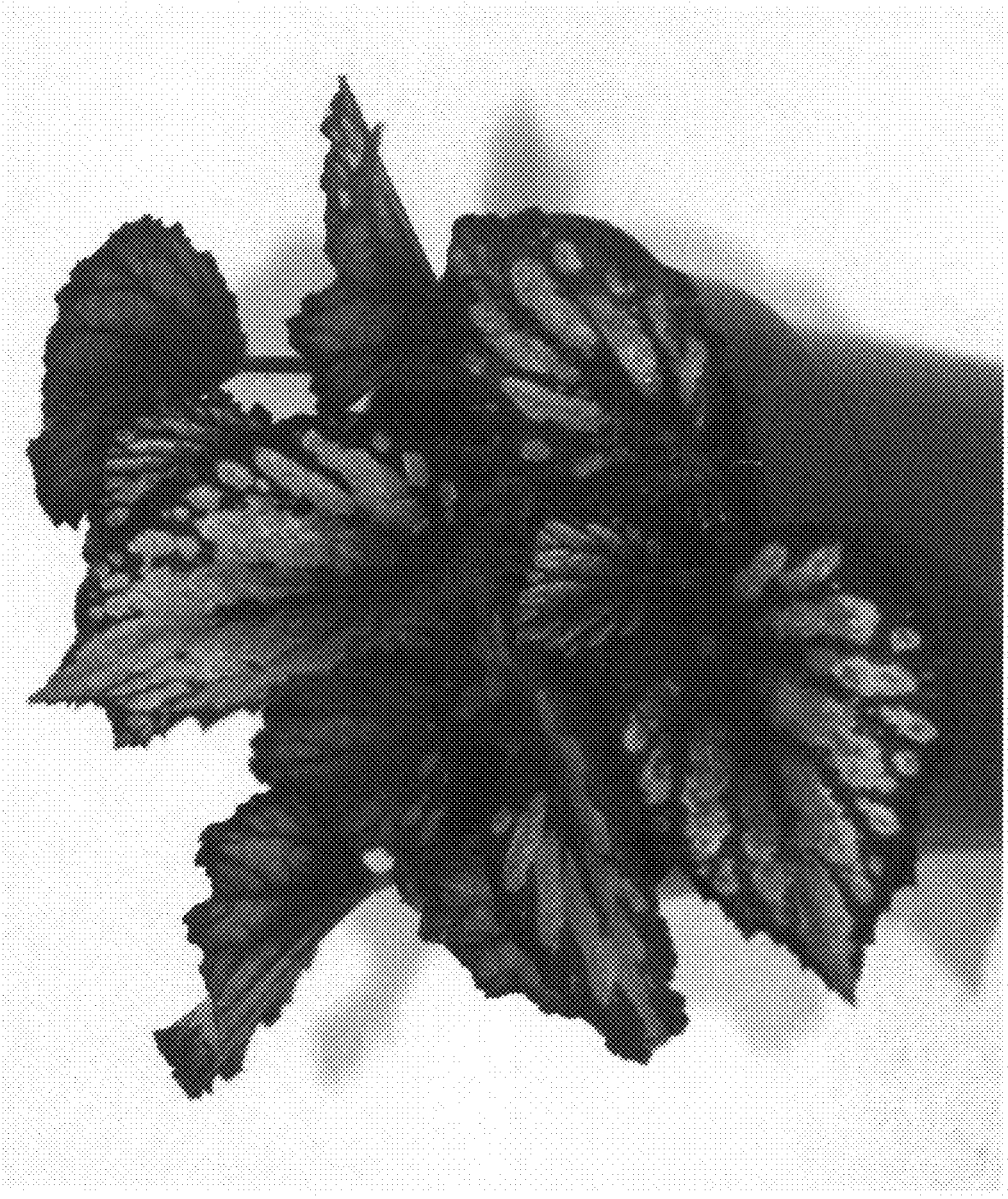

Latin name of the genus and species: *Begonia rex*.
Variety denomination: 'Salsa'.

BACKGROUND OF THE INVENTION

The new cultivar is the result of a planned breeding program of *Begonia rex*. The new variety originated from the crossing of the female parent, the unpatented variety of *Begonia rex* 'Valentine' with the pollen parent, the unpatented variety *Begonia hatacoa*. The crossing was made in September of 2004, by the inventor. The new variety was discovered by the inventor, Antoon Hoefnagels, a citizen of the Netherlands, in the summer of 2005 at a commercial greenhouse in Lent, the Netherlands.

After selecting and isolating the new cultivar, asexual reproduction of the new cultivar 'Salsa' was first performed in the same commercial greenhouse by vegetative cuttings in the winter of 2005. 'Salsa' has since produced several generations and has shown that the unique features of this cultivar are stable and reproduced true to type.

SUMMARY OF THE INVENTION

The cultivar 'Salsa' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Salsa.' These characteristics in combination distinguish 'Salsa' as a new and distinct *Begonia* cultivar:

1. Vibrant red/purple and silver/green foliage color.
2. Medium sized leaves, appropriate for commercial containers.
3. Full growth habit appropriate for commercial containers.
3. Easy branching, and rooting, resulting in easier commercial propagation.

PARENTAL COMPARISON

Plants of the new cultivar 'Salsa' are similar to the seed parent 'Valentine' in most horticultural characteristics. However, 'Salsa' differs in producing thicker, more leathery foliage that resists damage, whereas 'Valentine' has soft foliage that is susceptible to damage. Plants of 'Salsa' differ from the pollen parent in that the pollen parent has green foliage, with a different leaf blade shape.

COMMERCIAL COMPARISON

Plants of the new cultivar 'Salsa' are best compared to the unpatented commercial variety 'Merry Christmas.' Plants of 'Salsa' are similar to 'Merry Christmas' in most horticultural characteristics, however, Salsa has brighter colored foliage, smaller, narrower leaves and an overall more compact plant habit.

BRIEF DESCRIPTION OF THE PHOTOGRAPH

The accompanying photograph in FIG. 1 illustrates in full color a typical plant of 'Salsa' grown indoors in Camarillo, Calif. This plant is approximately 12 weeks old, shown in a 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'Salsa' plants grown indoors in Camarillo, Calif. during the Winter and Spring months. Temperatures ranged from Approximately 15° C. to 20° C. at night to 15° C. to 25° C. during the day. No artificial light, photoperiodic treatments or chemical treatments were given to the plants. Measurements and numerical values represent averages of typical plant types.

Botanical classification: *Begonia rex* 'Salsa'
Age of the plant described: Approximately 12 weeks.

Container size of the plant described: 4 inch commercial container.

PROPAGATION

Time to initiate roots: Summer: 20 to 25 days at approximately 20° C.

Root description: Fine, densely branched, non-fibrous, non-fleshy, colored near Grey-Brown N199A.

PLANT

Growth habit: Upright, slightly mounding.

Pot size of plant described: 4 inch.

Height: Approximately 12 cm from soil line to top leaf.

Plant spread: Approximately 20 cm.

Growth rate: Moderate.

Branching characteristics: Basal clumps formed.

Length of primary lateral branches: No actual branches, individual leaves arise from base. Please see petiole description.

Quantity of basal clumps: Approximately 3 clumps with 4 to 6 leaves per clump at 24 weeks.

FOLIAGE

Leaf:

*Arrangement.*—Rosette.

*Average length.*—6.2 cm.

*Average width.*—5.8 cm.

*Shape of blade.*—Cordate.

*Apex.*—Acuminate.

*Base.*—Cordate.

*Margin.*—Denticulate, crisped and ciliate.

*Texture of top surface.*—Shiny, leathery.

*Pubescence.*—Sparsely hispid, upper surface hairs mainly on veins, lower surface hairs entirely on veins.

*Aspect.*—Slightly concave from mid-vein.

*Color.*—Young foliage upper side: Background color, near Greyed-Green 191C. heavy blotches near Green 137A. Strong blush starting at the petiole attachment over approximately 50% of leaf colored near Red-Purple 61A. Margin, and large blotching near petiole attachment near Greyed-Green N189A. Young foliage under side: Background color, near RHS Greyed-Green 195A. heavy blotches starting at the petiole attachment over approximately 20% of leaf colored near Greyed-Purple 187A. Margin, near Greyed-Purple 187A Mature foliage upper side: Background color, near Green 137A. heavy blotches near Greyed-Green 191C, Strong blush starting at the petiole attachment over approximately 30% of leaf colored near Red-Purple 71A. Margin, and large blotching near petiole attachment near Greyed-Green N189A. Mature foliage under side: Near RHS Greyed-Green 191B. Some blotching near petiole attachment colored near Greyed-Purple 187B. Margin colored near Greyed-Purple 187A.

*Venation.*—Type: Pinnate. Venation color upper side: Takes on the same color as the leaf blade. Venation color under side: Near RHS Red-Purple 59A, closer to apex Red-Purple 59B. Closer to Base near Greyed-Purple 187B and 187C.

*Petiole.*—Length: Approximately 4 cm. Diameter: Approximately 0.4 cm. Color: Near RHS Greyed-Red 181C, lighter closer to leaf attachment, near 181D, darker near base, near 181A. Surface: Sparsely vilous. Hairs colored near RHS White 155C, approximately 0.3 cm long, fine and undulating.

*Stipule description.*—Shape: Deltoid. Length: Approximately 1.2 cm. Diameter: Approximately 0.5 cm at widest point. Color: Near RHS N155C with heavy coloration near main vein near Greyed-Purple 184B. Texture: Smooth.

FLOWER

Flowering not observed to date in this variety.

OTHER CHARACTERISTICS

Seeds and fruits: Not observed to date.

Disease/pest resistance: Neither resistance nor susceptibility to normal diseases and pests of *Begonia*.

Temperature tolerance: The new variety tolerates temperatures from approximately −2° C. to 35° C.

What is claimed is:

1. A new and distinct cultivar of *Begonia rex* plant named 'Salsa' as herein illustrated and described.

* * * * *